US006215853B1

United States Patent
Kump et al.

(10) Patent No.: US 6,215,853 B1
(45) Date of Patent: Apr. 10, 2001

(54) APPARATUS AND METHOD FOR X-RAY COLLIMATOR SIZING AND ALIGNMENT

(75) Inventors: Kenneth Scott Kump, Waukesha; John Edward Dwyer, Jr., Muskego, both of WI (US); Richard Aufrichtig, Mountain View, CA (US); Dale T. Duemer, Menomonee Falls; John E. Bechthold, Waukesha, both of WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/342,686

(22) Filed: Jun. 29, 1999

(51) Int. Cl.[7] ..................................................... G21K 1/04
(52) U.S. Cl. ........................................... 378/151; 378/147
(58) Field of Search ................................. 378/151, 152, 378/150, 99, 105, 147, 145, 160, 65; 250/511, 512, 513, 402, 468

(56) References Cited

U.S. PATENT DOCUMENTS

| | | | |
|---|---|---|---|
| 4,152,604 | * 5/1979 | Burbury | 250/402 |
| 4,361,902 | * 11/1982 | Brandt et al. | 378/152 |
| 5,572,567 | 11/1996 | Khutoryansky et al. | . |
| 5,636,259 | 6/1997 | Khutoryansky et al. | . |
| 5,654,996 | * 8/1997 | Steinberg et al. | 378/65 |
| 5,680,430 | 10/1997 | Khutoryansky et al. | . |
| 5,734,694 | 3/1998 | Khutoryansky et al. | . |
| 5,751,788 | 5/1998 | Khutoryansky et al. | . |
| 5,768,336 | 6/1998 | Khutoryansky et al. | . |

* cited by examiner

Primary Examiner—David V. Bruce
Assistant Examiner—Irakli Kiknadze
(74) Attorney, Agent, or Firm—McAndrews, Held & Malloy, Ltd.

(57) ABSTRACT

The present invention provides a method and apparatus for calibrating the size and alignment of a collimator. The method includes the step of acquiring a digital image showing collimator blades in front of a region of interest. The method then determines the position of one or more of the collimator blades or collimator assembly shown in the digital image. The method subsequently adjusts the position of one or more collimator blades toward a predetermined position with respect to the region of interest. Calibration may iterate until the collimator exposes a region of interest to within a predetermined tolerance.

34 Claims, 3 Drawing Sheets

APPARATUS AND METHOD FOR X-RAY COLLIMATOR SIZING AND ALIGNMENT

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention generally relates to medical diagnostic imaging systems, and in particular to X-ray collimator sizing and alignment in an X-ray imaging system employing a solid state X-ray detector.

Conventional X-ray imaging has found wide use in the medical diagnostic imaging industry. X-ray imaging systems are commonly used to capture, as examples, thoracic, cervical, spinal, cranial, and abdominal images that often include the information necessary for a doctor to make an accurate diagnosis. When having a thoracic X-ray image taken, for example, a patient stands with his or her chest against an X-ray sensor as an X-ray technologist positions the X-ray sensor and an X-ray source at an appropriate height. The X-ray energy generated by the source and attenuated to various degrees by different parts of the body, passes through the body and is detected by the X-ray sensor. An associated control system (where the X-ray sensor is a solid state imager) scans the detected X-ray energy and prepares a corresponding diagnostic image on a display. If the X-ray sensor is conventional film, the film is subsequently developed and displayed using a backlight.

Regulatory requirements mandate that imaging systems limit the X-ray field generated by the X-ray tube to an area that the X-ray sensor can acquire. X-ray imaging systems therefore use a collimator between the X-ray tube and the patient to constrain the X-ray field. To this end, the collimator may be constructed using horizontal and vertical lead blades that form an opening accurately corresponding to the X-ray sensor or desired anatomical area. During system calibration one must insure that the collimator blades can not be positioned at a size or orientation that allows imaging outside of the X-ray sensor. Furthermore, it is also of great importance that the horizontal and vertical blades are centered within the area of the X-ray sensor. These safeguards are required to prevent undesirable or unnecessary exposure of the patient to X-ray energy, and to insure excellent image quality.

In the past, however, the X-ray sensor was an X-ray sensitive screen and film combination. During system calibration a field engineer manually estimated the collimator sizing and centering using a field light positioned within the collimator. The field engineer then verified the calibration by exposing and developing the film. If measurements taken on the developed film indicated inappropriate collimator positioning, then the field engineer had to repeat the calibration process, after using a mechanical linkage and a screwdriver to manually adjust the collimator blade sizing and alignment. In the past, it was not uncommon for a single attempt at collimator calibration to require 5 or 6 minutes or more, and, taking into account repetition to ensure correct collimator sizing and alignment, as much as 30 minutes or more to finish calibration for a single size of film. Because most X-ray imaging systems are flexible enough to use numerous sizes and orientations of film (e.g., 14×17 and 17×14, 11×14 and 14×11, 8×10 and 10×8, as well as 5×7 and 7×5 inches), the field engineer required a significant amount of time to perform a complete collimator calibration. In addition, every calibration resulted in wasted film that could have been used to capture a diagnostic image for a doctor, and the accuracy attainable through manual collimator sizing and alignment was limited by human error.

A need has long existed for a method and apparatus for X-ray collimator sizing and alignment that overcomes the disadvantages discussed above and others previously experienced.

SUMMARY OF THE INVENTION

A preferred embodiment of the present invention provides a method for calibrating the size and alignment of a collimator. The method includes the step of acquiring a digital image showing collimator blades in front of a region of interest. An X-ray solid state image sensor typically obtains the image, and the region of interest may correspond, for example, to a desired image or exposure size on the image sensor. The method then determines the position of one or more of the collimator blades or collimator assembly shown in the digital image. To this end, the method may determine the width between pairs of blades, as well as the rotation associated with one or more of the blades. The method may then adjust the position of one or more collimator blades to expose the region of interest. Calibration may proceed over any predetermined number of exposure sizes.

A preferred embodiment of the present invention also provides a collimator calibration subsystem. The calibration subsystem includes a communication interface that exchanges data with collimator blade sensors, collimator blade actuators, and an image sensor. The calibration processor preferably includes a central processor coupled to a memory and the communication interface. The memory may include instructions for acquiring a digital image from the image sensor that shows the collimator blades in front of a region of interest, instructions for determining the position of the collimator blades, and instructions for adjusting a position of a collimator blade to expose the region of interest. Both the method and apparatus of the preferred embodiment may iteratively acquire an image, determine the position of the collimator blades, and adjust the positions of the collimator blades until the collimator reaches a predetermined size and alignment within a predetermined degree of accuracy.

DETAILED DESCRIPTION OF THE PREFERRED EMBODIMENT

Figure 1:
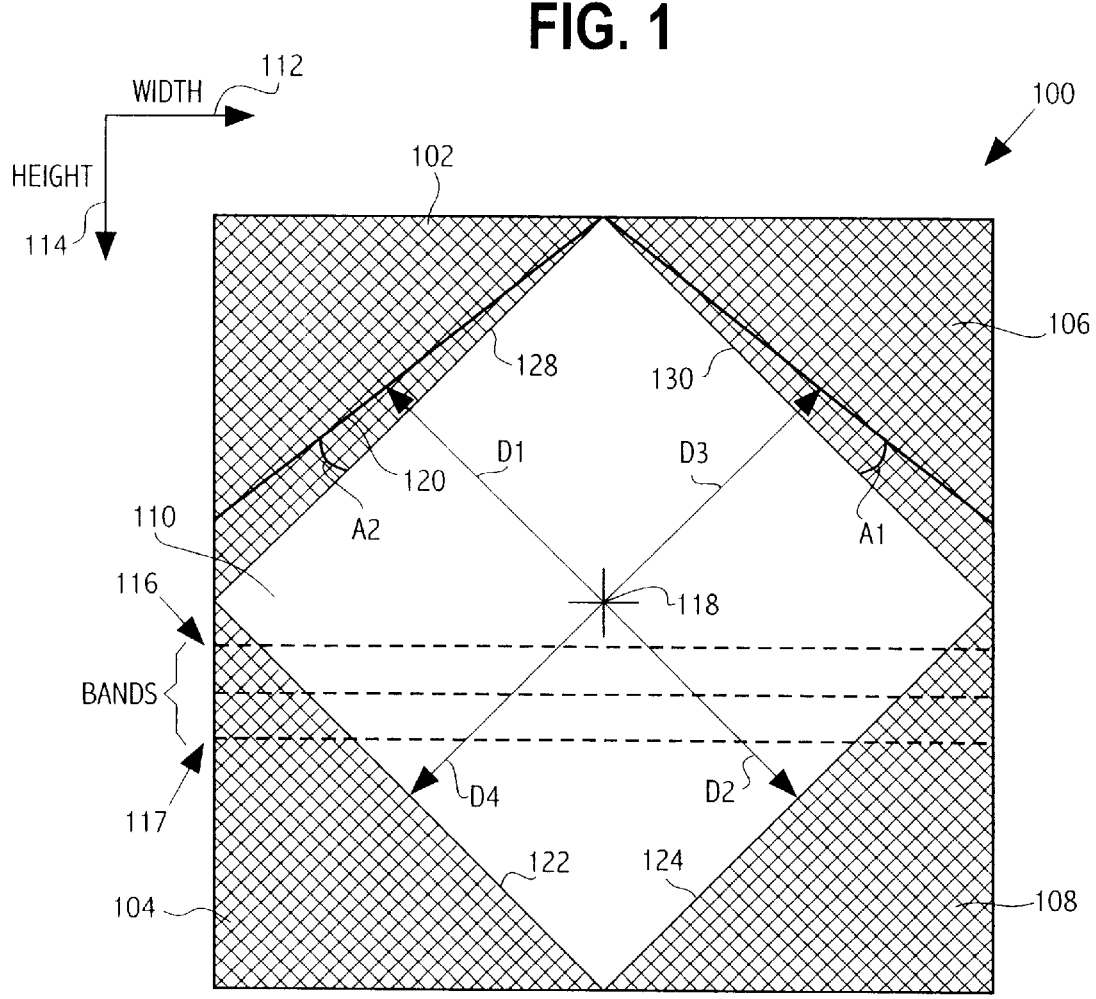
FIG. 1 illustrates a digital image of a collimator and several variables of interest in determining collimator sizing and alignment.

Turning to FIG. 1, that figure shows a digital image 100 of a collimator as well as the variables of interest in determining collimator size and alignment and the positions of the individual collimator blades. The image 100 shows first, second, third, and fourth collimator blades 102–108 in front of a region of interest 110. The digital image 100 has a corresponding width axis 112 and height axis 114 and, during processing, is preferably divided parallel to the width axis 112 into horizontal bands over the entire digital image height. FIG. 1 illustrates exemplary bands 116 and 117. FIG. 1 also illustrates the distances D1, D2, D3, D4, and angles A1 and A2, which are defined with respect to the image center 118, the collimator blade edges 120–126, and the region of interest 110. Two edges of the region of interest 110 are specifically identified as a first region edge 128 and a second region edge 130. It is noted that the region of interest may be of any predetermined geometric shape (e.g., square, rectangular, hexagonal, or triangular) and that more or fewer than four collimator blades may be may be controlled to expose a region of interest as described below.

The distances D1–D4 give the distance from the image center 118 to each corresponding collimator blade edge 120–126. As the collimator blades 102–108 translate during calibration, the distances D1–D4 change. The angles A1 and A2 give the angle between the collimator blade edges 120 and 126 and the first and second region edges 128 and 130, respectively, of the predetermined region of interest 110. As the collimator blades 102–108 rotate during calibration, the angles A1 and A2 change. For illustrative purposes, FIG. 1 shows only angles A1 and A2. However, the apparatus and method of the preferred embodiment may determine and adjust angles or rotations associated with any of the collimator blades 102–108, or the collimator as a whole. During calibration for an 11×14 inch exposure, for example, the collimator blades may be adjusted such that D1+D2=14 (preferably D1=D2=7), D3+D4=11 (preferably D3=D4=5.5), and A1=A2=0 within a predetermined tolerance (e.g., between 1 and 10%). In general, the collimator blades 102–108 may rotate and/or translate until they touch other collimator blades. Thus, the precise extent to which the collimator blades 102–108 may move varies according to the current collimator blade 102–108 positions and is not illustrated in FIG. 1. Angles A1 and A2 do, however, show a certain amount of rotation in the collimator blades 102, 106 away from the region of interest 110.

The region of interest 110 may correspond to any desired film or exposure size (for example, 11×14 inches). As shown in FIG. 1, the collimator is preferably rotated approximately 45 degrees with respect to the detector capturing the image. The rotation allows the detector to capture the edges of each blade in the collimator assembly. The rotation, however, is not limited to 45 degrees, but may range over a wide spectrum of angles that allows the detector to capture one or more collimator blade edges of interest for calibration. After calibration, the rotation in the collimator assembly may be manually or automatically reversed.

Figure 2:
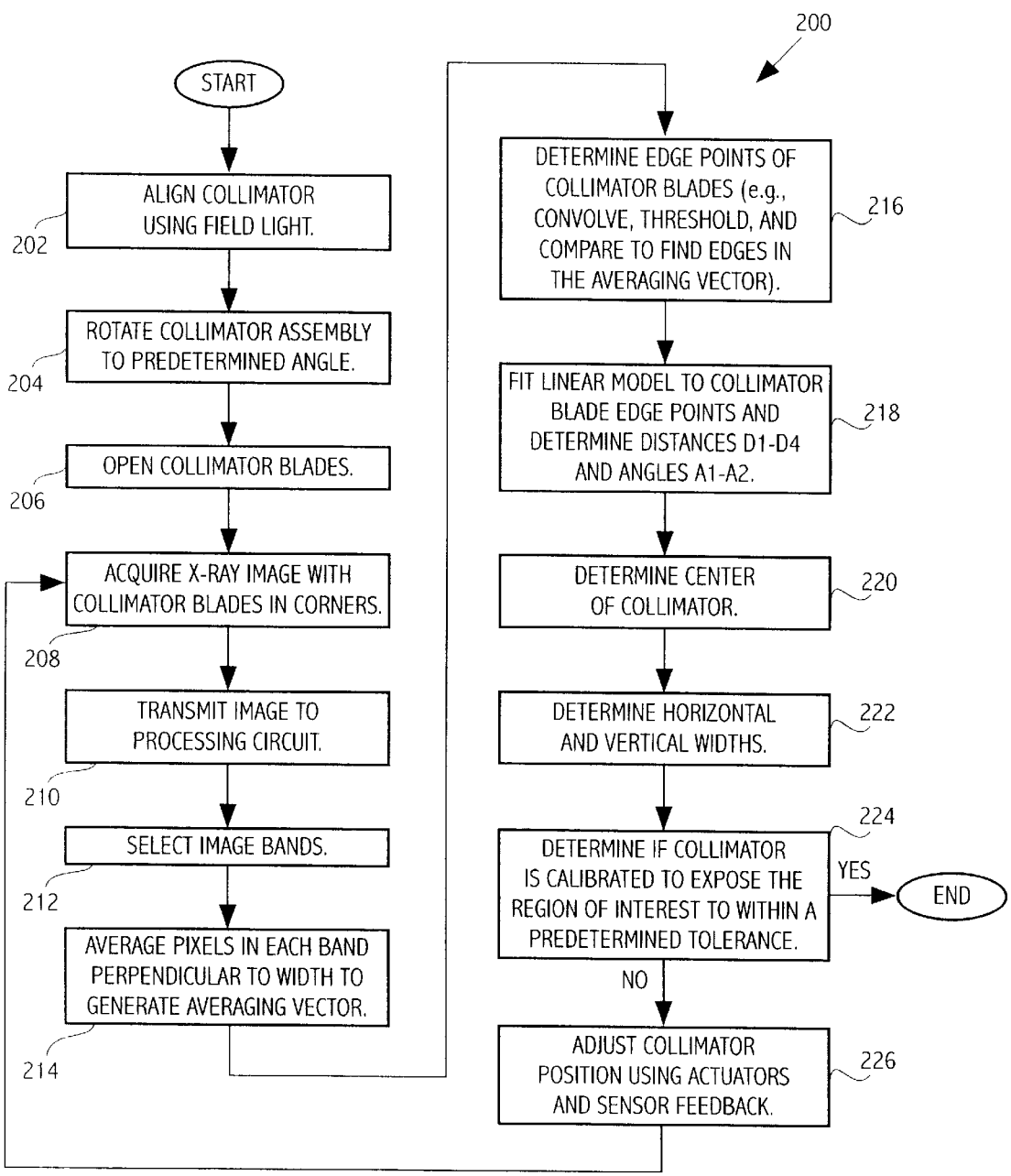
FIG. 2 illustrates a flow diagram of the steps performed during collimator sizing and alignment.

Turning next to FIG. 2, that figure shows a flow diagram 200 of the processing steps executed to size and align collimator blades. At step 202, the collimator is adjusted (e.g., by a field engineer), to a first rough approximation over the region of interest. The field light included with a collimator assembly may be used for this purpose. Next, at step 204, the collimator assembly is rotated to a predetermined angle with respect to the region of interest. As noted above, the angle is preferably 45 degrees, although other angles that show one or more collimator blade edges are also suitable. At step 206, the calibration processor (discussed below with reference to FIG. 3) opens the collimator blades to the extent required to fully expose the region of interest. As an example, the calibration processor may open the collimator blades to their fullest extent to calibrate exposures for the largest image size allowed by the detector. After the calibration processor finishes calibration of the largest image size, the calibration processor may proceed to the next smallest image size. The calibration processor may perform the calibration for various regions of interest in any desired order, however.

Next, at step 208, the calibration processor acquires from the detector an image that shows the collimator blades. The detector may be, for example, a solid state digital X-ray detector. The calibration processor reads the digital image 100 out of the solid state digital X-ray detector for processing (step 210). The calibration processor then preferably determines the positions of the collimator blades from the digital image 100 using any suitable image processing technique.

As an example and as indicated at step 212, the calibration processor may segment the digital image 100 into bands (e.g., bands 116, 117) across the width axis 112 of the digital image 100. As one example, the digital image may be 2048 pixels in height and width, and the bands 116, 117 may be 100 pixels in height. A wide range of variation is possible, however. For example, in a 2048×2048 pixel image, a band height in the range of 2–200 pixels is generally suitable. At step 214, the calibration processor averages the pixels in each horizontal band perpendicular to the width axis 112 (i.e., along the height axis 114) for every column in the band. The result is an averaging vector with as many elements (of averaged pixels) as there are columns in the band (e.g., 2048 elements when the digital image 100 is 2048 pixels wide). Continuing at step 216, the calibration processor locates the collimator blade edges by determining the derivative of image cross sections (or by using any other established mathematical edge response function). As an example, the calibration processor may convolve a kernel (e.g., a [−1, 1] or [−1, 0, 1] kernel) with the averaging vector, thereby generating a differentiated vector whose elements represent edge strength. Thresholding may then be applied to the edge strength elements to eliminate weak or small values from consideration. The edge strength elements are subsequently examined to find the largest change between elements (expected to occur between the collimator blade and the region of interest), thereby locating the collimator blade edge at a particular pixel location in the band. With the collimator blade edge located in each band, the calibration processor preferably determines, using a linear regression, the line along which the collimator blade edges lie (step 216). Once the calibration processor locates the lines determining the collimator blade edges, the calibration processor, at step 218, may directly determine position information including the quantities D1–D4 and A1–A2 using the known digital image 100 center location 118, and the known desired region of interest 110.

At step 220, the calibration processor preferably determines additional position information, including the center of the collimator, using the ratios D1/D2 and D3/D4 (which will both be exactly 1 if the collimator is exactly centered around the image center 118). The calibration processor also preferably determines the horizontal and vertical widths between collimator blades (step 222) as D1+D2 and D3+D4, respectively and assuming 45 degree rotation of the collimator assembly.

At step 224, the calibration processor determines if the collimator blade positions, as measured, expose the known region of interest to within a predetermined tolerance. If so, the calibration process for the region of interest ends, and the calibration processor may continue to calibrate other regions of interest. If not, the calibration processor, at step 226, uses one or more collimator blade actuators (which perform translation (e.g., linear transverse or longitudinal motion)

and rotation of the collimator blades and associated sensors (which provide feedback related to the degree of rotation or translation of the collimator blades) to adjust the position of the collimator blades. Although commonly available sensors and actuators are typically precise enough to adjust the collimator blades to the desired location upon command, processing may nonetheless loop back to step 208. The calibration processor thereby has the opportunity to reacquire the digital image and determine if the collimator is indeed calibrated correctly.

Figure 3:
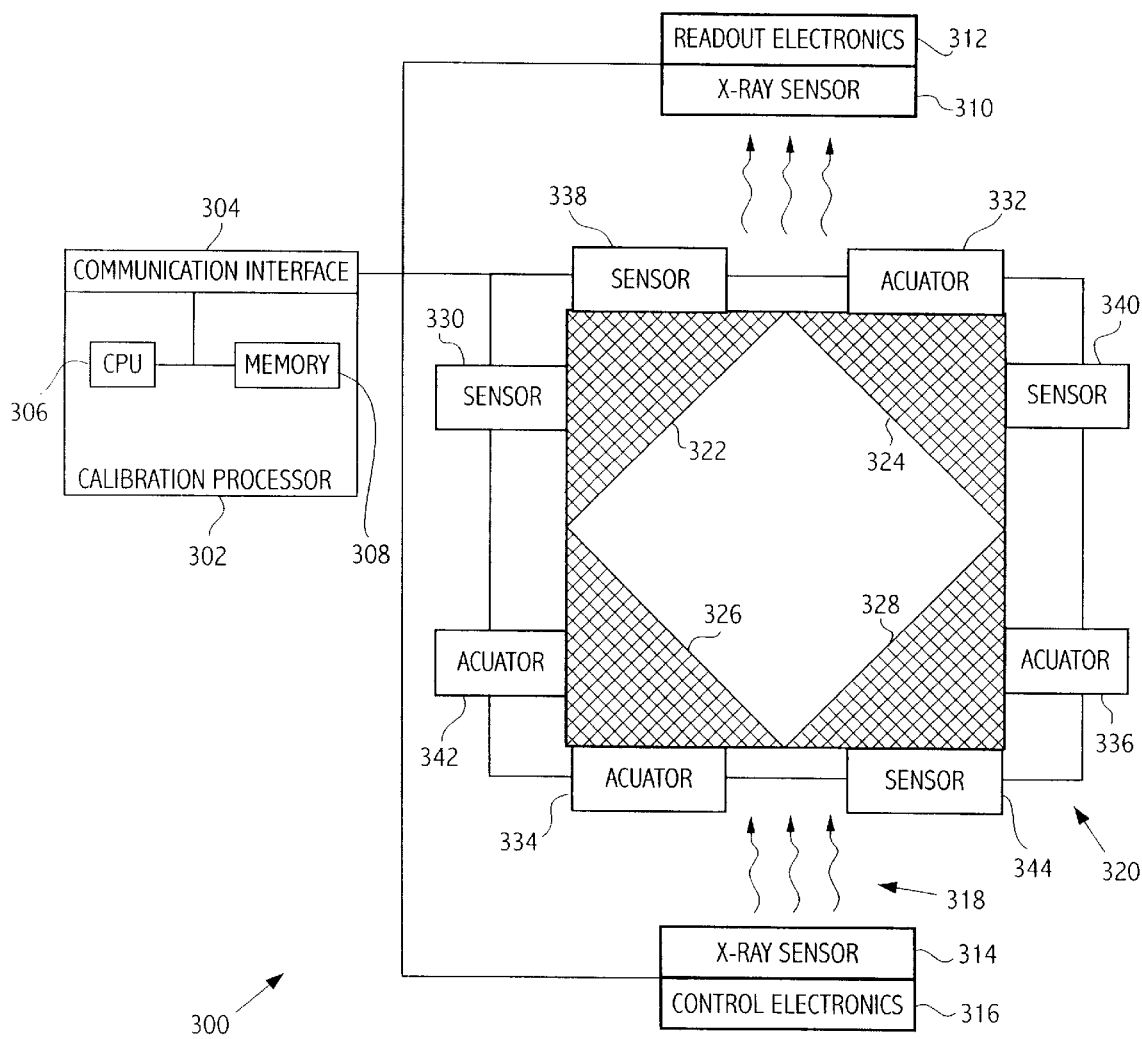
FIG. 3 shows a block diagram of an apparatus for collimator sizing and alignment.

Turning next to FIG. 3, that figure shows one embodiment of a calibration system 300, including a calibration subsystem 302 (also referred to as a calibration processor 302). The calibration processor includes a communication interface 304, a CPU 306, and a program/data memory system 308. Connected to the communication interface 304 is an X-ray sensor 310 (and associated readout electronics 312) and an X-ray source 314 (and associated control electronics 316). The X-ray source 314 generates X-ray energy 318 which passes through the collimator 320 to be detected by the X-ray detector 310. The collimator 320 includes collimator blades 322–328. The collimator blades 322–328 are associated with actuators 330–336 and position sensors 338–344. It will be appreciated that the collimator 320 is shown in a highly schematic view in FIG. 3 and that the collimator is in practice placed parallel to the X-ray detector 310 between the X-ray source 314 and a patient.

The X-ray detector is preferably a solid state X-ray detector, available, for example, from General Electric, Waukesha, Wis. The X-ray source 314 and control electronics 316 may be found in commercially available X-ray tube assemblies. Numerous possibilities exist for implementing the sensors 338–344 and actuators 330–336. For example, the sensors may be capacitive, inductive, potentiometer based or encoder based sensors that produce a signal proportional to the collimator position. The actuators use the sensor signals to adjust the collimator blade positions (or the collimator as a whole) through rotation and/or translation to the command positions, and may be implemented, for example, as electric, hydraulic, or pneumatic actuators.

The calibration processor 302 uses the communications interface 304 to assert activator signals that induce translation and rotation of the collimator blades (through their associated actuators). The activator signals may, for example, cause rotation or translation by a predetermined increment, or may rotate or translate the collimator blade in one motion completely through a desired change in position. The communications interface 304 may be any general purpose communications interface, including a serial, parallel, industrial, or network interface. The CPU 306 may be a general purpose CPU or an Application Specific Integrate Circuit that executes a calibration program stored in the memory system 308. The calibration program preferably follows at least the flow diagram steps 206–226 shown in FIG. 2. When the CPU 306 completes a calibration, the CPU 306 may then store collimator calibration information in the memory system 308 for future reference and retrieval. The collimator calibration information may include, for example, the position information (e.g., translation and/or rotation) associated with each collimator blade used to expose one or more regions of interest. In addition, the calibration information may also include least squares fit parameters (e.g., a slope and intercept value) for the collimator blade positions over several calibrations of various regions of interest. The CPU 306 may then quickly estimate new collimator blade positions for a new region of interest directly from the least squares fit model.

The present invention thereby provides a method and apparatus that provide fully automated accurate calibration of an X-ray collimator. The positioning may occur before patient exposure, or, for example, during imaging of a calibration phantom or the like. Undue waste of time, money, and resources associated with developing X-ray film are eliminated. The present invention further simplifies the collimator calibration process, and helps ensure that X-ray imaging systems meet regulatory requirements on the limitation of the X-ray field.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method for calibrating a collimator, the method comprising:

acquiring a digital image representative of collimator blades aligned relative to a region of interest;

automatically determining a position of at least one collimator blade from the digital image; and automatically adjusting a position of at least one collimator blade relative to the region of interest.

2. A method as recited in claim 1, wherein the step of acquiring the digital image comprises acquiring a digital image with a solid state X-ray detector.

3. A method as recited in claim 1, wherein the step of automatically determining position comprises segmenting at least a portion of the digital image into at least one band along an axis, and determining an edge of the collimator blades based on an edge response function.

4. A method as recited in claim 1, wherein the step of automatically determining position comprises fitting a collimator blade edge in the digital image with a linear model.

5. A method as recited in claim 3, wherein the step of automatically determining position further comprises fitting a collimator blade edge in the digital image with a linear model.

6. A method as recited in claim 4, wherein the step of automatically determining position comprises determining a distance from a center of the digital image to a collimator blade edge.

7. A method as recited in claim 1, wherein the step of adjusting a position of at least one collimator blade comprises at least one of translating and rotating at least one collimator blade relative to a reference point.

8. A method as recited in claim 1, wherein the step of adjusting a position of at least one collimator blade comprises adjusting at least one of a width between collimator blades and a centering of the collimator blades in the digital image.

9. A method as recited in claim 1, further comprising the steps of rotating a collimator assembly so that the collimator blades appear in the region of interest, and reversing the rotation after calibration is completed.

10. A method according to claim 1, further comprising the step of iterating the acquiring, determining, and adjusting steps until the collimator blades expose the region of interest within a predetermined tolerance.

11. A collimator calibration subsystem comprising:

a communication interface for carrying at least one collimator blade position sensor signal, at least one collimator blade actuator signal, and an image detector signal; and a central processor, coupled to the communication interface, for automatically determining a position of a collimator blade based on an image detector signal, and for automatically generating a blade activator signal for adjusting a position of a collimator blade toward a desired position relative to the region of interest.

12. A collimator calibration subsystem according to claim 11, further comprising at least one sensor and at least one actuator for at least one collimator blade.

13. A collimator calibration subsystem according to claim 11, wherein the communication interface connects to a digital X-ray detector image detector.

14. A collimator calibration subsystem according to claim 11, wherein the processor segments at least a portion of the digital image into at least one band along an axis, averages pixels in each band perpendicular to the axis, and determines edges of the collimator blades using an edge response function.

15. A collimator calibration subsystem according to claim 11, wherein the processor fits a linear model to determine blade edges in the digital image with a linear model.

16. A collimator calibration subsystem according to claim 14, wherein the processor fits a linear model to determine collimator blade edges in the digital image with a linear model.

17. A collimator calibration subsystem according to claim 11, wherein the activator signal induces at least one of translation and rotation of at least one collimator blade using an actuator.

18. A collimator calibration subsystem according to claim 11, wherein the activator signal adjusts at least one of a width between collimator blades and a centering of the collimator blades in the digital image.

19. A collimator calibration subsystem according to claim 11, further comprising a memory coupled to the processor, and wherein the processor stores calibration position information for at least one collimator blade in the memory.

20. A collimator calibration subsystem according to claim 11, wherein the processor iterates the determining and generating steps until the collimator blades expose the region of interest to within a predetermined tolerance.

21. A collimator calibration subsystem according to claim 11, wherein the activator signal induces movement of the collimator blade by a predetermined increment, after which the processor determines a new position of the collimator blade.

22. A collimator calibration subsystem according to claim 11, wherein the processor determines current and destination calibrated positions of the collimator blade, and asserts the activator signal to move the collimator blade from the current position to the destination calibration position.

23. A collimator calibration system comprising:
an X-ray detector;
at least one collimator blade located relative to an region of interest;

a detector for detecting a position of the collimator blade;

a blade position controller for moving the collimator blade through at least one of a rotation and a translation; and a calibrator for determining the position of collimator blades and automatically instructing the blade position controller to move the collimator blade.

24. A collimator calibration system of claim 23 wherein the calibrator directs the blade position controller to move the collimator blade by a predetermined increment, after which the calibrator determines a new position of the collimator blade.

25. A collimator calibration system of claim 23, wherein the calibrator calculates current and destination calibrated positions of the collimator blade, and instructs the blade position controller to move the collimator blade from a current position to the destination calibration position.

26. A collimator calibration subsystem according to claim 23, further comprising at least one sensor and at least one actuator for at least one collimator blade.

27. A collimator calibration subsystem according to claim 23, further comprising a communication interface coupled to the X-ray detector, the blade position controller, and the calibrator.

28. A collimator calibration subsystem according to claim 23, wherein the calibrator segments at least at portion of the digital image into at least one band along an axis, averages pixels in each band perpendicular to the axis, and determines edges of the collimator blades using an edge response function.

29. A collimator calibration subsystem according to claim 23, wherein the calibrator fits a linear model to determine blade edges in the digital image with a linear model.

30. A collimator calibration subsystem according to claim 28, wherein the calibrator fits a linear model to determine collimator blade edges in the digital image with a linear model.

31. A collimator calibration subsystem according to claim 23, wherein the blade position controller generates an activator signal that induces at least one of translation and rotation of at least one collimator blade using an actuator.

32. A collimator calibration subsystem according to claim 23, wherein the blade position controller adjusts at least one of a width between collimator blades and a centering of the collimator blades in the digital image.

33. A collimator calibration subsystem according to claim 28, wherein the axis lies in a width direction of the digital image.

34. A collimator calibration subsystem according to claim 23, wherein the calibrator iterates the determining and instructing until the collimator blades expose the region of interest to within a predetermined tolerance.

* * * * *